(12) United States Patent
Jach et al.

(10) Patent No.: US 6,692,625 B1
(45) Date of Patent: Feb. 17, 2004

(54) ELECTROCHEMICAL SENSOR

(75) Inventors: Olaf Jach, Böblingen (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/101,175

(22) PCT Filed: Nov. 3, 1997

(86) PCT No.: PCT/DE97/02538
§ 371 (c)(1),
(2), (4) Date: Dec. 30, 1998

(87) PCT Pub. No.: WO98/20334
PCT Pub. Date: May 14, 1998

(30) Foreign Application Priority Data

Nov. 6, 1996 (DE) .......................... 196 45 684
Oct. 23, 1997 (DE) .......................... 197 46 743

(51) Int. Cl.[7] ................................ G01N 27/26
(52) U.S. Cl. ........................................ 204/426
(58) Field of Search ................ 204/421–429

(56) References Cited

U.S. PATENT DOCUMENTS

| 4,272,349 | A | * | 6/1981 | Furutani et al. | 204/429 |
|---|---|---|---|---|---|
| 4,402,820 | A | * | 9/1983 | Sano et al. | 204/425 |
| 4,502,939 | A | * | 3/1985 | Holfelder et al. | 204/426 |
| 4,851,103 | A | | 7/1989 | Usami et al. | |
| 5,130,002 | A | * | 7/1992 | Murase et al. | 204/426 |
| 5,169,513 | A | * | 12/1992 | Mase et al. | 204/425 |
| 5,314,604 | A | * | 5/1994 | Friese et al. | 204/426 |
| 5,507,937 | A | | 4/1996 | Renz et al. | |
| 5,522,979 | A | | 6/1996 | Tatumoto et al. | |
| 5,676,811 | A | * | 10/1997 | Makino et al. | 204/426 |
| 5,763,763 | A | * | 6/1998 | Kato et al. | 204/412 |
| 6,007,688 | A | * | 12/1999 | Kojima et al. | 204/429 |

* cited by examiner

*Primary Examiner*—Jill Warden
(74) *Attorney, Agent, or Firm*—Kenyon & Kenyon

(57) ABSTRACT

Electrochemical sensor for measuring a gas concentration of a sampled gas with an electrochemical element, including an electrochemical pump cell with a first and a second electrode and with a gas chamber which is connected to the sampled gas via a gas inlet opening and in which one of the two electrodes is located, with the gas inlet opening being covered by a porous covering. Also a method for producing an electrochemical sensor of this type.

2 Claims, 2 Drawing Sheets

ELECTROCHEMICAL SENSOR

FIELD OF THE INVENTION

The present invention relates to a sensor, in particular to an electrochemical sensor.

Electrochemical sensors of the generic type are known. These conventional electrochemical sensors include an electrochemical element which has an electrochemical pump cell with a preferably flat first solid-electrolyte body and a first and second preferably porous electrode. These sensors further include an electrochemical sensor cell, connected to the pump cell, with a preferably flat second solid-electrolyte body and a third and fourth preferably porous electrode, as well as a diffusion resistor arrangement connected to the sampled gas chamber via a gas inlet opening and a gas inlet duct and surrounded by the two solid-electrolyte parts, i.e. located in an inner cavity. The diffusion resistor arrangement can be filled with a porous substance. The sampled gas enters the inner cavity via the gas inlet opening and the gas inlet duct, with the first and second electrodes of the pump cell regulating the entry of the sampled gas into the cavity, thereby producing a controlled partial pressure on the gas component to be measured. Power is supplied to the electrochemical pump cell by a device mounted outside the electrochemical element.

Due to the different partial pressures of the gas in the diffusion resistor arrangement and in a reference gas chamber located, for example, in the second solid-electrolyte body, an electrochemical potential difference occurs between the electrodes of the second solid-electrolyte body and is measured by a voltmeter unit positioned outside the electrochemical element.

Another coventional method provide the electrochemical sensor with an electrical heater which heats both the electrochemical pump cell and the electrochemical sensor cell in order to ensure a suitable operating temperature for the electrochemical sensor.

The layout of the electrochemical sensor known from conventional methods has a disadvantage in that liquid components contained in the sampled gas, for example drops of gasoline in the exhaust gas of an internal combustion engine, and solid components, for example particles of soot, can enter the inner cavity through the gas inlet opening of the electrochemical sensor and interfere with the function of the electrochemical sensor over a long period of time. The measured value determined by the electrochemical sensor can be corrupted by exhaust gas that has been enriched with gasoline ("rich" exhaust gas). Clogging of the gas inlet opening can even cause the electrochemical sensor to break down.

SUMMARY OF THE INVENTION

The present invention relates to an electrochemical sensor for measuring a gas concentration, for example an oxygen concentration, of a sampled gas which has an electrochemical element, including an electrochemical pump cell with a first and a second electrode and with an inner gas chamber which is connected to the sampled gas via a gas inlet opening and located in one of the two electrodes, with the gas inlet opening being covered by a porous covering. The present invention offers the advantage of preventing liquid and solid components contained in the sampled gas from penetrating the interior of the sensor, i.e. the inner cavity referred to as the gas chamber. This is done by applying a porous layer to the surface of the electrochemical element facing the sampled gas chamber as a covering for the gas inlet opening. This covering is permeable to the sampled gas, yet presents a barrier to the liquid and solid components contained in the sampled gas. The liquid held back by and deposited in this covering, for example gasoline, quickly evaporates after a heater, which is preferably provided, is turned on, so that only gasoline vapor is forced out of the interior of the electrochemical sensor by the gas, for example oxygen, which is continuously being pumped by the electrochemical pump cell.

The present invention also relates to a method for producing this type of electrochemical sensor in which the gas inlet opening is first created and subsequently covered with a covering layer. The porous covering is finally applied to this additional covering layer. This advantageously ensures that the application of a porous covering does not impair the porosity characteristics and thus the operability of the electrochemical sensor.

The covering layer can itself be porous, i.e. permeable to the sampled gas. However, materials that burn without leaving residue under heat treatment or pore-forming materials are advantageously used for the covering layer. If pore-forming materials are used, an additional protective membrane remains after producing the electrochemical sensor according to the present invention, preferably after sintering. Suitable materials include wax, carbon black, graphite, methyl xanthines such as theobromine, theophylline or caffeine. The covering layer is preferably applied by a transfer technology, while the porous covering is preferably applied by screen printing.

According to a further advantageous embodiment of the present invention, a hollow space is created in the gas inlet duct which is advantageously partially filled with a porous substance, i.e. between the covering provided on the gas inlet opening and a porous filling advantageously located in the inner cavity. The hollow space prevents capillary migration of the liquid gasoline from the covering according to the present invention to the inner porous filling. This hollow space, which thus forms a barrier between the porous covering and the porous filling located in the inner cavity, can be preferably formed by burning out sublimatable material during sintering. The covering on the gas inlet opening is preferably made of a porous material which can be a continuation of the porous protective layer covering the entire surfaces of the electrochemical element facing the sampled gas chamber.

In to another advantageous embodiment, the present invention relates to dual-cell sensors (broad-band sensors) which have a pump cell, including a first solid-electrolyte body, and concentration cell, including a second solid-electrolyte body.

DETAILED DESCRIPTION OF THE DRAWINGS

Figure 1:
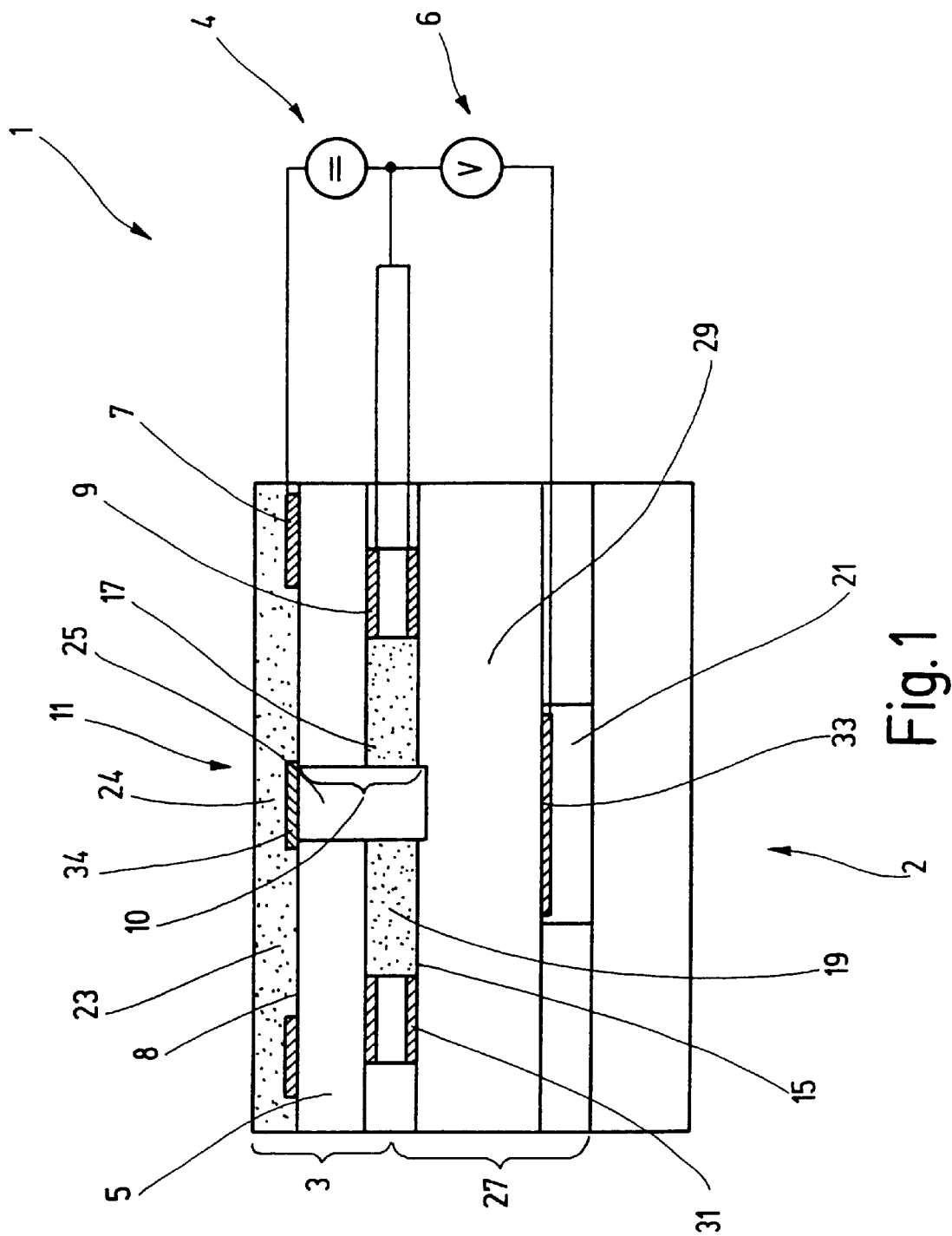
FIG. 1 shows a schematic cross-section of an electrochemical sensor according to the present invention.

FIG. 1 shows a cross section of an electrochemical sensor 1 having an electrochemical element 2, a power supply unit 4 and a voltmeter 6. Electrochemical element 2 includes an electrochemical pump cell 3 which is constructed from a first flat solid-electrolyte body 5, a first porous electrode 7, and a second porous electrode 9. Electrochemical element 2 also includes an electrochemical sensor cell, referred to below as Nernst cell 27, which is constructed from second solid-electrolyte body 29 as well as from a third electrode 31 and a fourth electrode 33. Electrochemical pump cell 3 is supplied with power at first and second electrodes 7, 9 by external power supply unit 4. First and second solid-electrolyte bodies 5, 29 are connected to one another and enclose an inner cavity 15, also known as gas chamber 17. Inner cavity 15 is completely filled with a porous material 19 and contains second and third electrodes 9, 31. Inner cavity 15 comes into contact with sampled gas 13 via a gas inlet duct 10 and a gas inlet opening 11. Positioned over gas inlet opening 11 is a porous covering 24, which is part of a porous protective layer 23 covering surface 8 of first solid-electrolyte body 5 facing sampled gas 13, and therefore also covering first electrode 7 of electrochemical pump cell 3. An additional porous protective membrane 34 is located between porous covering 24 and gas inlet opening 11. Second solid-electrolyte body 29 has a reference gas chamber 21. Fourth electrode 33, which is exposed to a reference gas, is located in reference gas chamber 21.

Sampled gas 13 enters inner cavity 15 via gas inlet opening 11 and gas inlet duct 10, with a controlled partial pressure being set by pumping oxygen in and out using the pump voltage applied to first and second electrodes 7, 9 of pump cell 3. Power is supplied to electrochemical pump cell 3 by a power supply unit 4 mounted outside electrochemical element 2. Due to different partial pressures of the gas in gas chamber 17 and in a reference gas chamber 21 located in second solid-electrolyte body 29, an electrochemical potential difference, which is measured by a voltmeter 6 positioned outside the electrochemical element, is produced between third and fourth electrodes 31, 33 of second solid-electrolyte body 29.

Covering 24 according to the present invention and hollow space 25 located beneath covering 24 prevent liquid and solid components contained in the sampled gas, for example gasoline or particles of soot, from entering gas chamber 17 via gas inlet opening 11 and gas inlet duct 10. Covering 24 is designed as part of a porous protective layer 23 which is applied to at least part of surface 8 of first solid-electrolyte body 5 facing sampled gas 13. This porous protective layer 23 is permeable to sampled gas 13, yet presents a barrier to liquid and solid components contained in sampled gas 13. Hollow space 25 located beneath covering 24 prevents capillary migration of the gasoline to inner cavity 15 or gas chamber 17 via gas inlet duct 10. The gasoline held back by and deposited in covering 24 quickly evaporates after turning on a heater, which is preferably provided but not shown here, so that only gasoline vapor is forced out of inner cavity 15 of electrochemical sensor 1 by the gas, for example oxygen, being continuously pumped by electrochemical pump cell 3.

Figure 2:
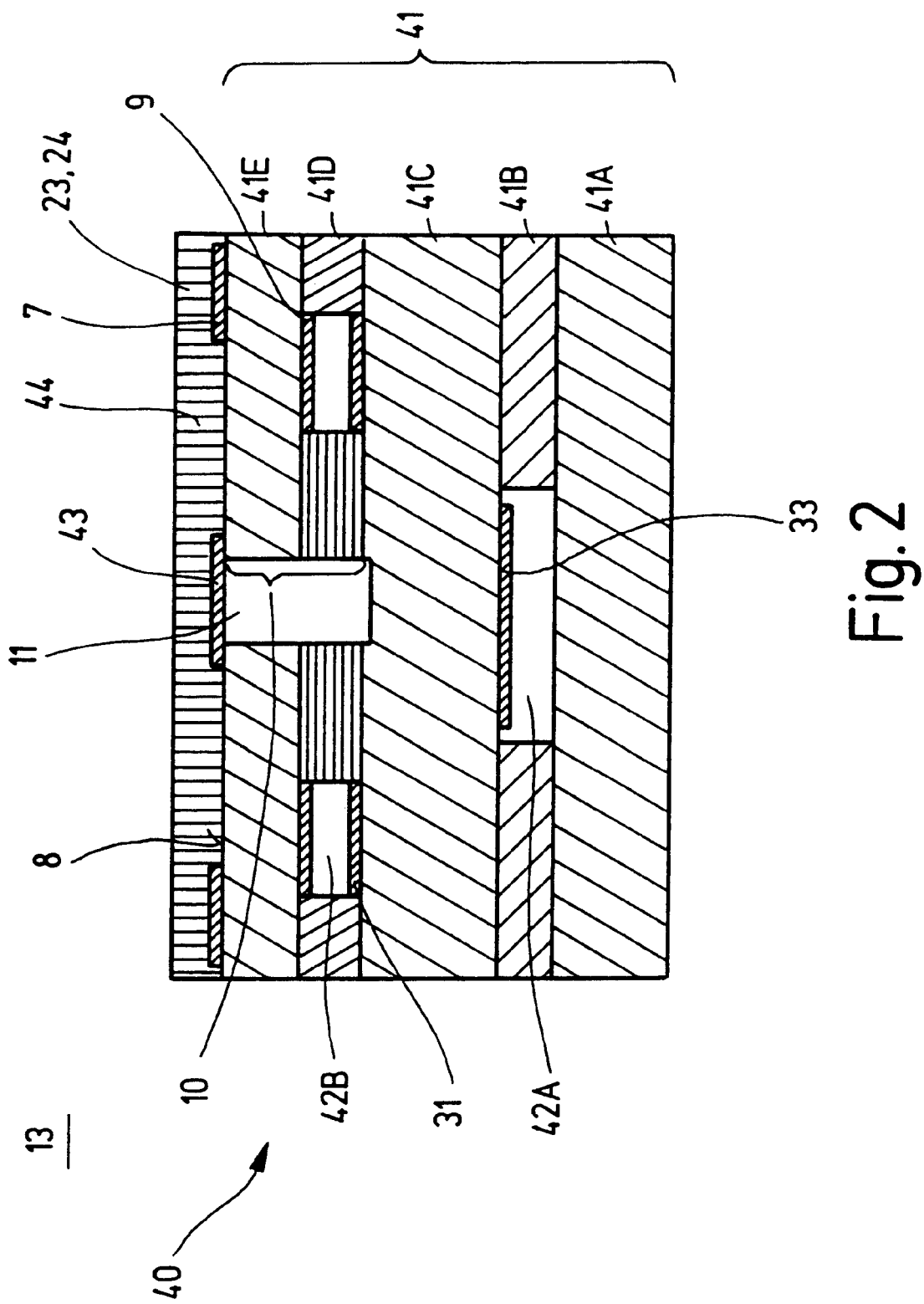
FIG. 2 shows a schematic cross-section, similar to the cross-section of FIG. 1, of a precursor body during production.

The production of electrochemical sensor 1 is described below with reference to FIG. 2. Second solid-electrolyte body 29 and first solid-electrolyte body 3 are made of ceramic materials produced by sintering a precursor green body 41. The precursor green body is produced by stacking individual, flat precursor green bodies 41A through 41E. During sintering, these green bodies 41A through 41E are transformed into a one-piece ceramic body. Green bodies 41B, 41D, and 41E have recesses 42A, 42B which form gas chamber 17 and reference gas chamber 21 after sintering. The electrodes are attached by coating the surfaces of individual green bodies 41C through 41E, for example by pressing. This method is generally known. Gas inlet duct 10 is created, for example drilled, after stacking green bodies 41A through 41E and before sintering. It can also be created by other suitable techniques, for example stamping the green bodies or treating them with lasers. Protective layer 23, which simultaneously serves as protective covering 24 for gas inlet opening 11 of gas inlet duct 10, is then applied to surface 8 facing the sampled gas. The protective layer is applied in the form of sinterable paste 44 by screen printing. This paste is transformed into porous protective layer 23 by the sintering process that follows.

In doing this, care must be taken to ensure that paste 44 does not penetrate gas inlet duct 10, because this would alter the porosity characteristics of sensor 2 and impair its operability. For this reason, a covering film in the form of a thin sheet 43 is applied using a transfer technology. This means that sheet 43 is located on a support. The support is placed on surface 8. Sheet 43 is transferred to surface 8 by the force exerted by the support.

Covering film 43 can also be applied by other technologies such as in the form of a screen printed film.

Sheet 43 closes gas inlet opening 11 so that paste 44 can be easily applied without entering gas inlet channel 10. During sintering, sheet 43 burns away without leaving a residue, forming a hollow space. Alternatively, during sintering, sheet 43 forms an additional thin porous protective membrane 34 through which sampled gas 13 can be diffused into gas inlet duct 10 without hindrance. This is shown in FIG. 1.

Sheet 43 can also itself form porous protective membrane 34 if it is made of a suitable material that is permeable to the sampled gas. This type of sheet would not be altered by the sintering process. A sheet of this type is also suitable for electrochemical sensors according to the present invention which are not subjected to sintering or similar heat treatment during production.

What is claimed is:

1. A method for producing an electrochemical sensor including an electrochemical pump cell having two electrodes and a gas chamber, the method comprising the steps of:

producing a gas inlet opening in the electrochemical sensor;

providing a sampled gas to the gas chamber of the electrochemical pump cell via the gas inlet opening;

completely covering the gas inlet opening with a covering layer, the covering layer being composed of one of: i) a pore-forming material, and ii) a material that burns without leaving a residue;

after the gas inlet opening is completely covered with the covering layer, applying a porous cover over the gas inlet opening so that the porous cover completely covers the gas inlet opening;

applying a heat treatment to the covering layer after the porous cover is applied; and allowing fluid communication between the gas chamber and the sampled gas via the gas inlet opening through the porous cover;

wherein the covering layer is composed of one of carbon black, graphite, wax, methyl xanthine, theophylline and caffeine.

2. The method according to claim 1, wherein the methyl xanthine includes theobromine.

* * * * *